(12) United States Patent
Sage et al.

(10) Patent No.: US 7,766,394 B2
(45) Date of Patent: Aug. 3, 2010

(54) BREAKAWAY CONNECTORS AND SYSTEMS

(75) Inventors: Shahn S. Sage, Andover, MN (US); Matthew H. Adams, Zimmerman, MN (US); Benjamin A. Johnson, Woodbury, MN (US); James Grant Skakoon, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 818 days.

(21) Appl. No.: 11/589,694

(22) Filed: Oct. 30, 2006

(65) Prior Publication Data

US 2008/0100061 A1 May 1, 2008

(51) Int. Cl.
*F16L 37/00* (2006.01)
(52) U.S. Cl. ................ 285/321; 285/318; 285/276; 604/905
(58) Field of Classification Search ............. 285/321, 285/318, 305, 276; 604/905, 256
See application file for complete search history.

(56) References Cited

U.S. PATENT DOCUMENTS

| | | | |
|---|---|---|---|
| 2,701,147 A | 2/1955 | Summerville | |
| 2,905,485 A | 9/1959 | Zajac | |
| 3,181,895 A | 5/1965 | Cator | |
| 3,447,819 A | 6/1969 | Borsum et al. | |
| 3,731,955 A | 5/1973 | Borsum et al. | |
| 3,918,679 A * | 11/1975 | Silvana | 251/149.1 |
| 4,004,298 A | 1/1977 | Freed | |
| 4,013,310 A | 3/1977 | Dye | |
| 4,193,616 A | 3/1980 | Sarson et al. | |
| 4,256,106 A * | 3/1981 | Shoor | 604/411 |
| 4,328,813 A | 5/1982 | Ray | |
| 4,350,159 A | 9/1982 | Gouda | |
| 4,366,945 A | 1/1983 | Bläuenstein | |
| 4,376,525 A * | 3/1983 | Fremy | 251/149.6 |
| 4,436,125 A * | 3/1984 | Blenkush | 141/330 |
| 4,526,572 A | 7/1985 | Donnan et al. | |
| 4,576,359 A | 3/1986 | Oetiker | |
| 4,606,564 A * | 8/1986 | Kurachi | 285/248 |
| 4,610,468 A | 9/1986 | Wood | |
| 4,613,112 A | 9/1986 | Phlipot et al. | |
| 4,752,292 A * | 6/1988 | Lopez et al. | 604/244 |
| 4,834,719 A | 5/1989 | Arenas | |

(Continued)

FOREIGN PATENT DOCUMENTS

DE 90 13 145.2 1/1991

(Continued)

OTHER PUBLICATIONS

U.S. Appl. No. 11/589,697, filed Oct. 30, 2006, Adams et al.

(Continued)

*Primary Examiner*—David E Bochna
(74) *Attorney, Agent, or Firm*—Mueting, Raasch & Gebhardt, P.A.

(57) ABSTRACT

A breakaway connector for use with a medical (e.g., catheter) or other fluid system. The connector may include two couplers that engage one another via a substantially frictionless retention device. In one embodiment, the retention device includes a biased cylindrical roller attached to one coupler that contacts an outer surface of the other coupler. The outer surface may include a grooved surface to receive the roller when the couplers are fully attached.

19 Claims, 10 Drawing Sheets

U.S. PATENT DOCUMENTS

| | | | |
|---|---|---|---|
| 4,890,866 A | | 1/1990 | Arp |
| 4,934,655 A * | | 6/1990 | Blenkush et al. ......... 251/149.1 |
| 5,120,085 A * | | 6/1992 | Shin ........................... 285/317 |
| 5,257,622 A | | 11/1993 | Hooper et al. |
| 5,294,092 A * | | 3/1994 | Wade et al. .............. 251/149.6 |
| 5,314,463 A | | 5/1994 | Camps et al. |
| 5,356,396 A | | 10/1994 | Wyatt et al. |
| 5,405,336 A | | 4/1995 | Austin et al. |
| 5,411,348 A | | 5/1995 | Balsells |
| 5,425,558 A * | | 6/1995 | Dennany, Jr. ................ 285/308 |
| 5,437,650 A * | | 8/1995 | Larkin et al. ................. 604/536 |
| 5,492,147 A * | | 2/1996 | Challender et al. ..... 137/614.05 |
| 5,527,358 A | | 6/1996 | Mehmanesh et al. |
| 5,545,152 A | | 8/1996 | Funderburk et al. |
| 5,609,584 A | | 3/1997 | Gettig et al. |
| 5,628,726 A * | | 5/1997 | Cotter ........................ 604/6.1 |
| 5,669,730 A * | | 9/1997 | Bidaux ........................ 285/316 |
| 5,820,614 A * | | 10/1998 | Erskine et al. .............. 604/905 |
| 5,908,447 A | | 6/1999 | Schroeppel et al. |
| 5,927,277 A | | 7/1999 | Baudino et al. |
| 6,112,121 A | | 8/2000 | Paul et al. |
| 6,508,789 B1 | | 1/2003 | Sinnott et al. |
| 6,517,115 B1 | | 2/2003 | Blivet |
| 6,776,638 B2 | | 8/2004 | Thurston |
| 6,827,693 B2 | | 12/2004 | White et al. |
| 6,902,207 B2 | | 6/2005 | Lickliter |
| 7,055,812 B2 | | 6/2006 | Balsells |
| 7,153,296 B2 * | | 12/2006 | Mitchell .................... 604/905 |
| 7,306,197 B2 * | | 12/2007 | Parrino et al. .............. 604/256 |
| 2004/0181249 A1 | | 9/2004 | Torrance et al. |
| 2004/0204690 A1 | | 10/2004 | Yashiro et al. |
| 2004/0210249 A1 | | 10/2004 | Fogarty et al. |
| 2005/0033371 A1 | | 2/2005 | Sommer et al. |
| 2005/0143714 A1 | | 6/2005 | Hegland et al. |
| 2005/0251102 A1 | | 11/2005 | Hegland et al. |
| 2005/0253389 A1 | | 11/2005 | Schulte |
| 2006/0127158 A1 | | 6/2006 | Olson et al. |
| 2006/0129126 A1 | | 6/2006 | Kaplitt et al. |
| 2006/0135945 A1 | | 6/2006 | Bankiewicz et al. |
| 2006/0195066 A1 | | 8/2006 | Cross, Jr. |
| 2006/0264814 A1 | | 11/2006 | Sage |
| 2006/0264911 A1 | | 11/2006 | Nelson |

FOREIGN PATENT DOCUMENTS

| | | |
|---|---|---|
| EP | 0678302 B1 | 2/1999 |
| FR | 2 614 386 | 10/1988 |
| GB | 2 343 723 A | 5/2000 |
| WO | WO 00/24462 | 5/2000 |
| WO | WO 03/090840 A1 | 11/2003 |
| WO | WO 03/090840 A1 | 7/2004 |
| WO | WO 2004/060466 A1 | 7/2004 |

OTHER PUBLICATIONS

International Preliminary Report on Patentability and Written Opinion of International Searching Authority for PCT/US2007/022824 (9 pgs).

"Flexible Fused Silica Capillary Tubing" datasheet [online]. Polymicro Technologies, LLC, Phoenix, Arizona, 2006 [retrieved on Feb. 20, 2007]. Retrieved from the Internet<URL:http://www.polymicro.com/products/capillarytubing/products_capillarytubing_tsp_tsg_tsu.htm>; 2 pgs.

Sanftner et al., "AAV2-mediated gene delivery to monkey putamen: evaluation of an infusion device and delivery parameters" *Experimental Neurology*, 2005; 194:476-483.

* cited by examiner

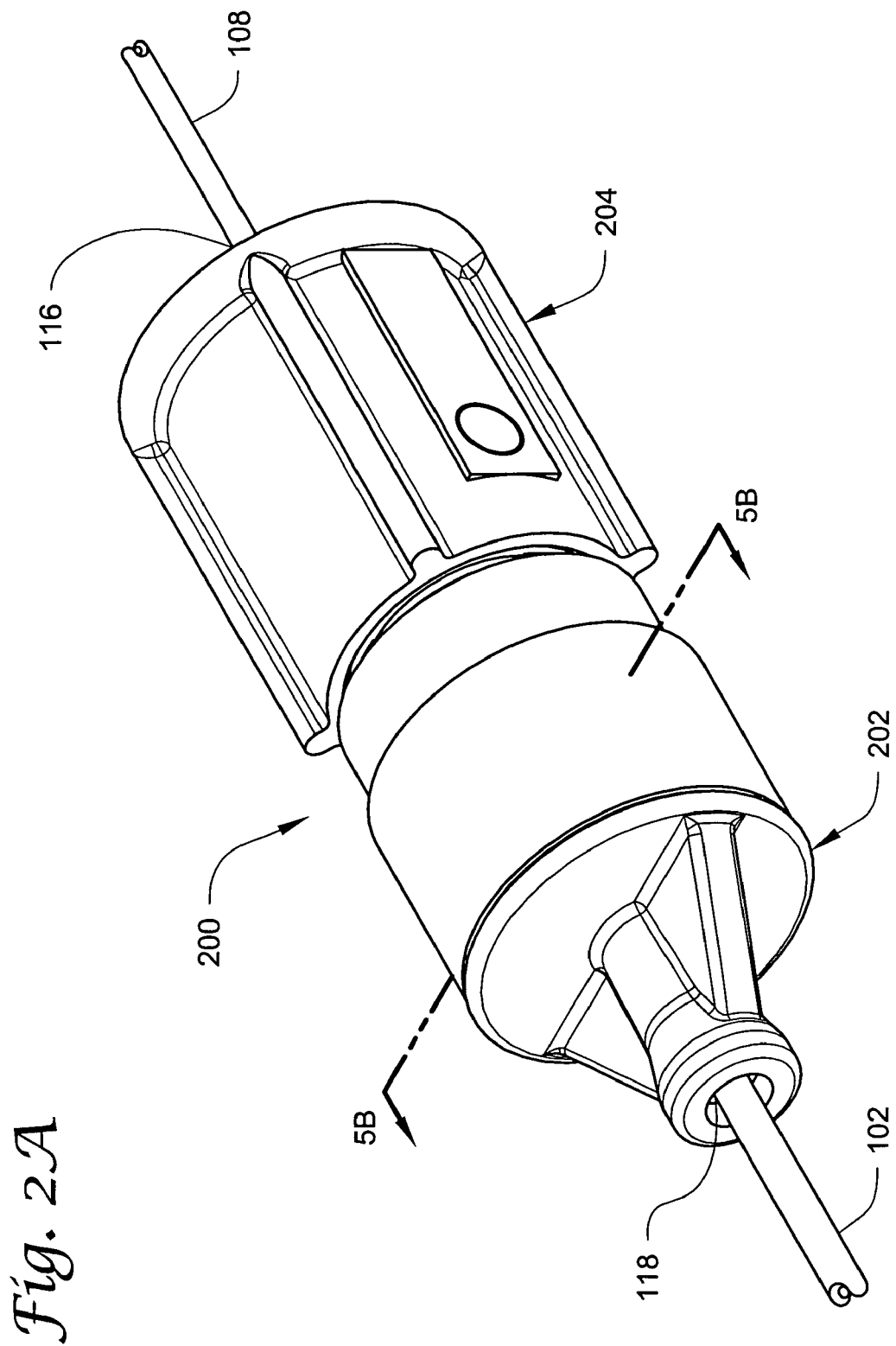

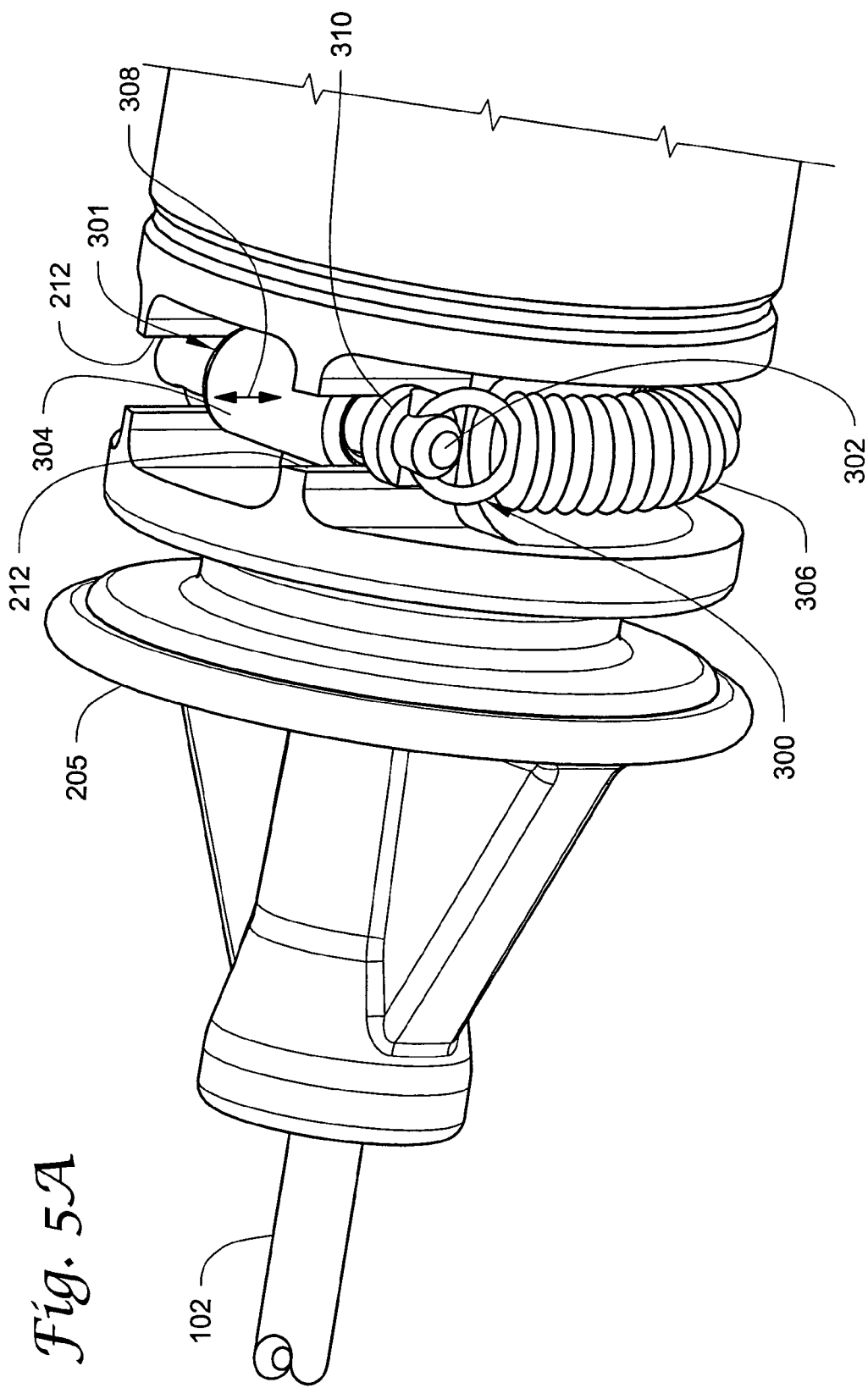

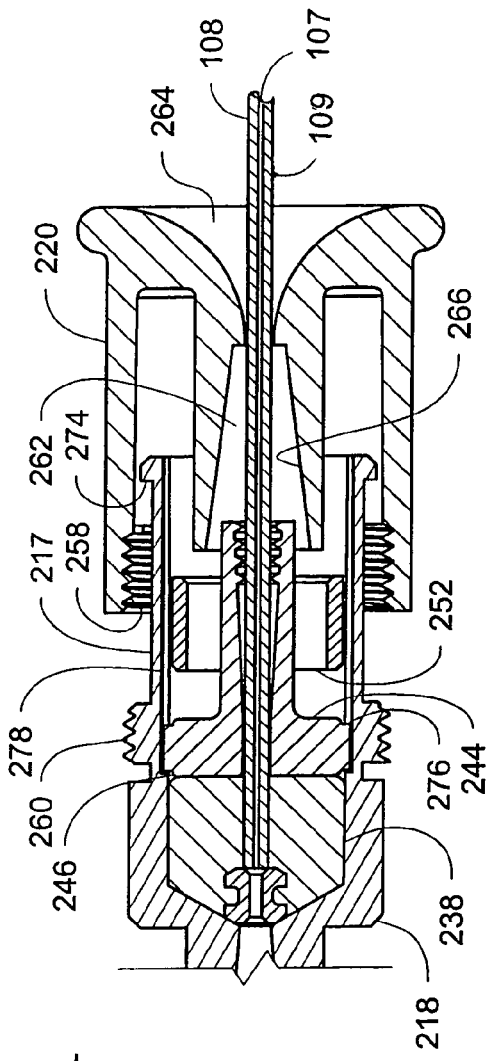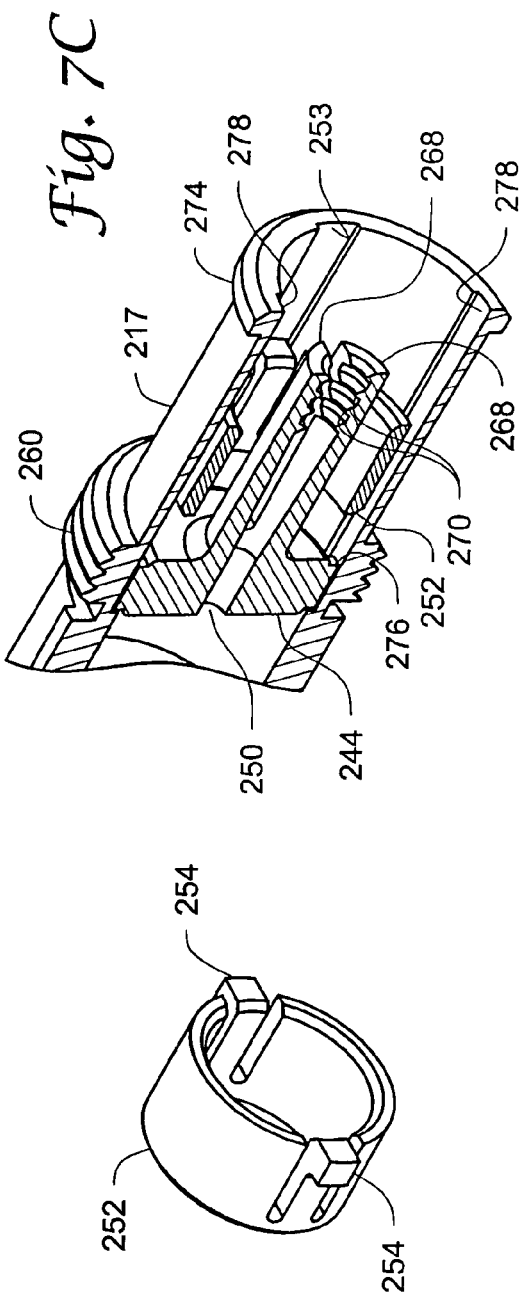

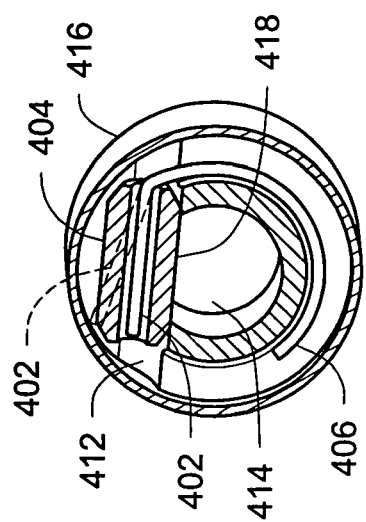
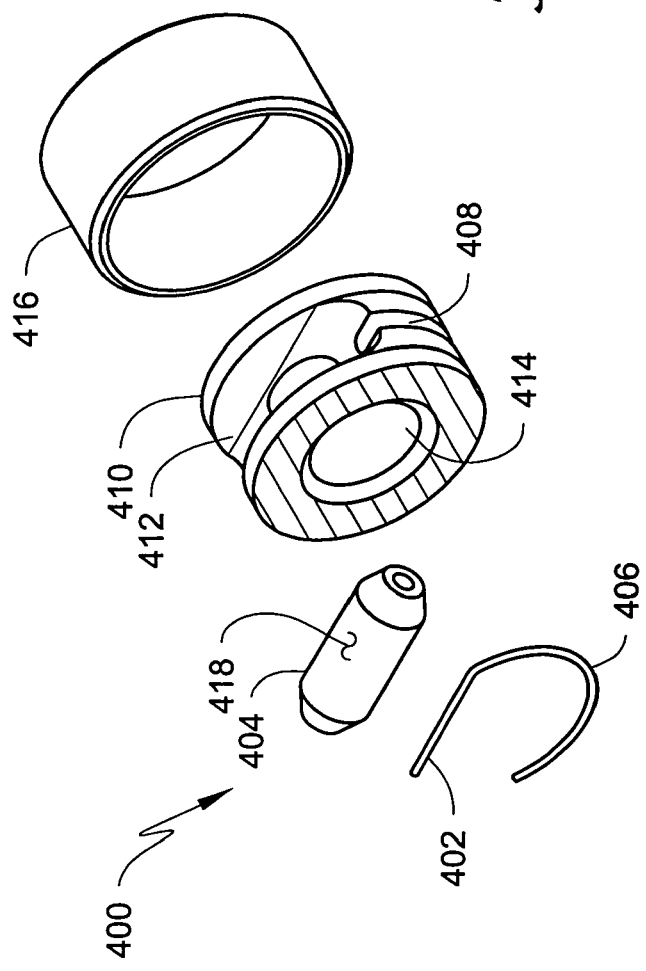

BREAKAWAY CONNECTORS AND SYSTEMS

TECHNICAL FIELD

The present invention relates generally to medical devices and, more particularly, to connectors and systems for coupling a first catheter to another device (e.g., to a secondary tube), wherein the connector is configured to release and separate once a threshold traction force is applied across the connector.

BACKGROUND

Medical procedures involving the delivery or removal of fluids from the body often utilize a catheter system for fluid transport. The catheter system may include a flexible tube or catheter that operatively enters the body, and an externally located fluid reservoir. One example of a removal catheter system is a urinary catheter for use with patients that may have difficulty urinating.

Other catheter systems are capable of delivering a fluid, e.g., a therapeutic agent, to the body. For example, the use of intracerebroventricular or parenchymal catheters is known for infusing therapeutic agents to a specific location within the brain to treat a variety of disorders. In an illustrative example, an incision is made in a patient's scalp to expose the skull through which a burr hole may then be formed. The catheter may then be inserted through the burr hole and anchored in place. To avoid unintended injury to the brain, surgeons typically use stereotactic apparatus/procedures to position brain instruments such as catheters and electrical leads. For example, U.S. Pat. No. 4,350,159 to Gouda illustrates an exemplary stereotactic instrument used to position an electrode.

To secure the catheter relative to the burr hole, burr hole anchor devices, including devices similar to those described in U.S. Pat. No. 4,328,813 to Ray and U.S. Pat. No. 5,927,277 to Baudino et al., may be used.

The portion of the catheter extending beyond the skull may be tunneled beneath the skin (e.g., to connect to an implanted reservoir or pump) or, alternatively, routed outside the body where it may connect, typically via a longer secondary tube, to an external source containing the therapeutic agent.

While completely implanted systems may be beneficial for the long term treatment of certain chronic ailments, external routing may be preferable for shorter term therapies (e.g., those lasting a few days or less). Such short term implantations may be beneficial for a variety of treatments including, for example, acute gene therapy (e.g., for the treatment of Parkinson's disease) and chemotherapy.

While current external routing configurations are satisfactory for their intended purpose, external catheter systems may present issues not necessarily present with internal systems. For example, the externalized components may benefit from various attachment and strain relief techniques to minimize movement of the implanted catheter that might result from exposure to inadvertent, external forces. Moreover, in the event of a catheter break, the externalized catheter system may require component replacement and/or additional sterilization procedures in order to reduce the risk of contamination. While such attachment techniques and sterilization procedures are effective, it may be beneficial if the need for such additional measures could be reduced or eliminated.

SUMMARY

The present invention may overcome these and other issues by providing, a connector that decouples the implanted catheter from the secondary tube once a threshold traction force is applied between the two members. In one embodiment, a connector for coupling a first tube to a second tube is provided. The connector includes a first coupler comprising an engagement portion; and a second coupler comprising a tubular body defining a bore to receive the engagement portion of the first coupler. A roller assembly associated with the second coupler is also included, wherein the roller assembly has a cylindrical roller that, in a first configuration, is offset from an axis of the second coupler. The cylindrical roller is configured to engage an outer surface of the engagement portion in rolling contact as the engagement portion translates within the bore of the tubular body.

In another embodiment, a medical tubing connector is provided that includes a first coupler attached to a first tube, wherein the first coupler includes an attachment member having an engagement portion. A second coupler attached to a second tube is also included, wherein the second coupler has a tubular body defining a bore to receive the engagement portion of the attachment member. The connector also includes a biased retention device attached to the second coupler and movable from a first configuration, wherein a contact surface formed by the retention device forms a secant extending through the bore of the second coupler, to a second configuration, wherein the contact surface of the retention device is located at or outside of the bore.

In yet another embodiment, a method for connecting a first tube to a second tube is provided. The method includes positioning a first coupler attached to the first tube proximate a second coupler attached to the second tube such that a bore of the second coupler is aligned with an engagement portion of the first coupler. The method further includes sliding the engagement portion of the first coupler into the bore of the second coupler, wherein a biased cylindrical roller associated with the second coupler contacts an engagement surface of the engagement portion. The method also includes engaging the cylindrical roller with a grooved surface formed in an outer surface of the engagement portion when the engagement portion is fully inserted into the bore of the second coupler.

The above summary is not intended to describe each embodiment or every implementation of the present invention. Rather, a more complete understanding of the invention will become apparent and appreciated by reference to the following Detailed Description of Exemplary Embodiments and claims in view of the accompanying figures of the drawing.

BRIEF DESCRIPTION OF THE VIEWS OF THE DRAWING

The present invention will be further described with reference to the figures of the drawing, wherein:

FIGS. 2A-2B illustrate enlarged perspective views of the connector of FIG. 1, wherein: FIG. 2A is an enlarged perspective view of the breakaway connector of FIG. 1; and FIG. 2B is an exploded perspective view illustrating how a modified connector may be attached to a headgear apparatus;

FIGS. 5A-5B illustrate an exemplary retention device, e.g., a roller assembly, for use with the connector of FIG. 2A, wherein: FIG. 5A is an enlarged perspective view of the roller assembly; and FIG. 5B is a section view taken along line 5B-5B of FIG. 2A;

FIGS. 7A-7C illustrate various aspects of the first coupler of FIG. 2A, wherein: FIG. 7A is a section view of the first coupler in a partially assembled state, the view taken through a plane containing an axis of the first coupler;

FIG. 7B is a perspective view of a stop member of the first coupler; and FIG. 7C is a partial perspective section view of a portion of the first coupler; and FIGS. 8A-8B illustrate a retention device in accordance with another embodiment of the invention, wherein: FIG. 8A is an exploded partial perspective view; and FIG. 8B is a perspective section view.

Figure 1:
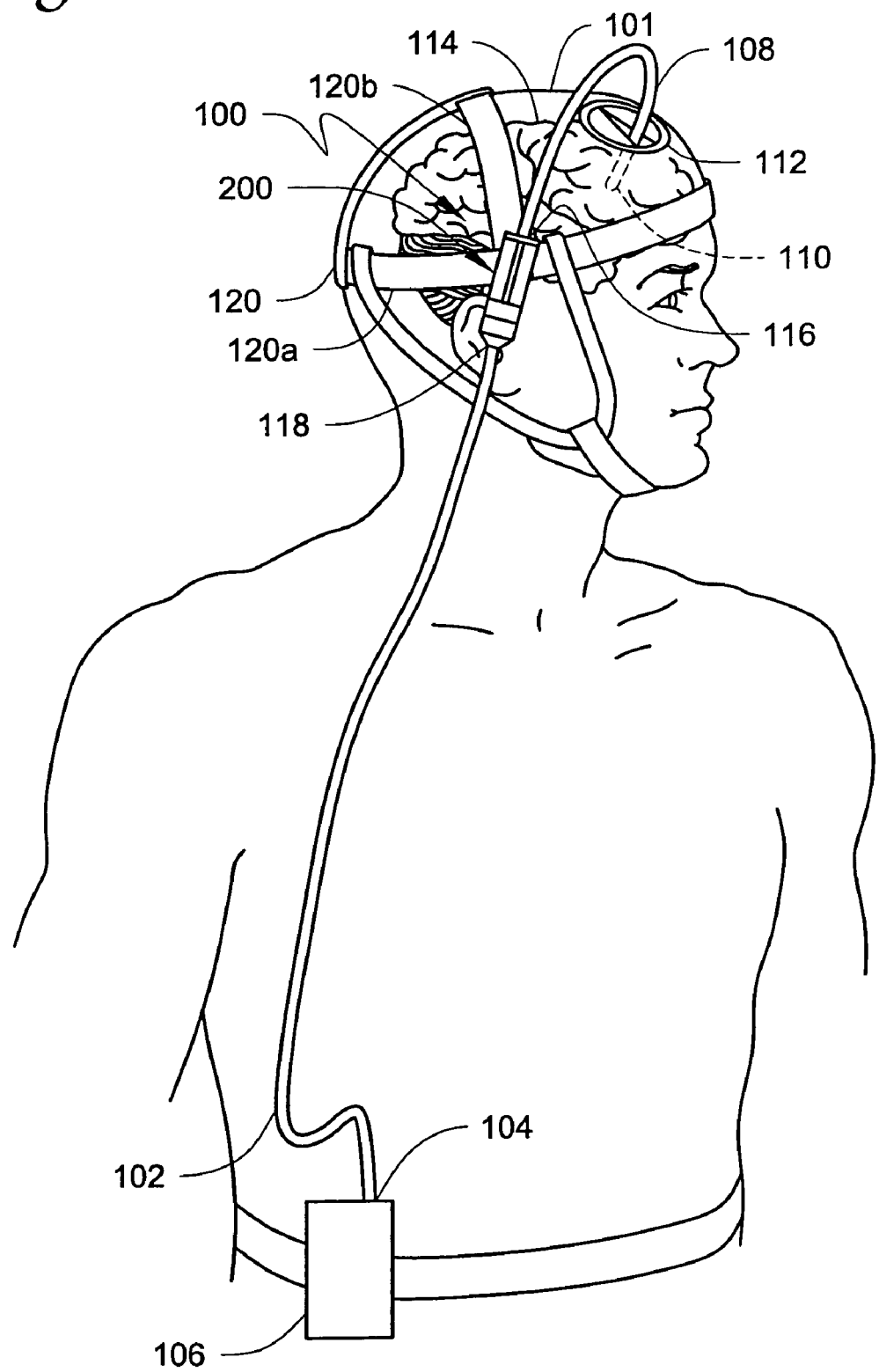
FIG. 1 illustrates an exemplary system, e.g., infusion system, as it may be attached to a patient's body, wherein the system incorporates a breakaway connector in accordance with one embodiment of the present invention, the connector coupling a first implanted catheter with a secondary external tube.

The figures are rendered primarily for clarity and, as a result, are not necessarily drawn to scale.

DETAILED DESCRIPTION OF EXEMPLARY EMBODIMENTS

In the following detailed description of illustrative embodiments of the invention, reference is made to the accompanying figures of the drawing which form a part hereof, and in which are shown, by way of illustration, specific embodiments in which the invention may be practiced. It is to be understood that other embodiments may be utilized and structural changes may be made without departing from the scope of the invention.

The present invention is directed generally to fluid coupling devices and, in particular, to medical connectors, systems, and methods for coupling a first tube (e.g., catheter) to a second tube or other medical device. In the illustrated embodiment, the connector is shown as part of a catheter, e.g., infusion, system having a partially implanted catheter and an external infusion pump. However, this configuration is not limiting as embodiments of the connectors and connector systems of the present invention may find use in other catheter applications, as well as in other medical and non-medical fluid systems.

Connectors in accordance with embodiments of the present invention are typically configured to separate or de-couple once a threshold traction force is applied across the connector (e.g., applied to the two tubes joined by the connector). As a result, the connector provides a "breakaway" function in the event of exposure to inadvertent forces. Preferably, two couplers of the connector engage one another via a low friction (e.g., substantially frictionless) retention device. In the embodiments described and illustrated herein, the connector may also maintain a closed fluid path, in the event of connector breakaway, to protect the implanted catheter from contamination.

It is noted that the terms "comprises" and variations thereof do not have a limiting meaning where these terms appear in the accompanying description and claims. Moreover, "a," "an," "the," "at least one," and "one or more" are used interchangeably herein.

Relative terms such as left, right, forward, rearward, top, bottom, side, upper, lower, horizontal, vertical, and the like may be used herein and, if so, are from the perspective observed in the particular figure. These terms are used only to simplify the description, however, and not to limit the scope of the invention in any way.

FIG. 1 illustrates an implantable medical system, such as a brain infusion catheter system 100, in accordance with one embodiment of the invention as it may be partially implanted within a patient's body 101.

The exemplary infusion system may include a first medical tube, e.g., brain catheter 108, and a second medical tube, e.g., secondary tube 102. The tube 102 may have its distal end 104 coupled to a reservoir (e.g., infusion pump 106, which may be identical or similar in construction to insulin pumps such as the Paradigm 515 or 715 pumps produced by Medtronic MiniMed of Northridge, Calif., USA) containing a volume of a therapeutic agent. Similarly, the brain catheter 108 may have its distal end 110 implanted within the body 101 (as used herein, the terms "distal" and "proximal" are taken from the reference of a connector 200 as shown in FIG. 1). In the illustrated example, the catheter 108 has its distal end 110 implanted, via a burr hole 112, at a predetermined location within the brain 114 of the patient. A burr hole anchor may be used to secure the catheter 108 relative to the burr hole 112. A proximal end 116 of the catheter 108 may extend outside the body 101 and connect to a corresponding proximal end 118 of the tube 102, e.g., via the connector 200.

The system 100 may, in one embodiment, be configured to deliver a therapeutic agent containing a virally mediated gene therapy as an acute treatment for Parkinson's disease. The therapeutic agent is delivered, via the tube 102 and catheter 108, to the brain 114. This application is not limiting, however, as the system may be configured to deliver most any therapeutic agent (e.g., chemotherapy) to most any area of the body without departing from the scope of the invention.

An enlarged view of the exemplary connector 200 is illustrated in FIG. 2A. The connector 200 may include a second coupler 202 attached to the secondary tube 102 and a first coupler 204 attached to the brain catheter 108 as further described below. In the illustrated embodiment, the first coupler 204 may be supported by an optional headgear apparatus 120 (see FIG. 1), which may hold the connector 200, e.g., via a connection with the first coupler, during implantation. While illustrated as supported by a headgear apparatus 120 in FIG. 1, the connector 200 could alternatively be generally unsupported, e.g., supported only by the free proximal ends 116 and 118 of the catheter 108 and tube 102, respectively, without departing from the scope of the invention. An exemplary system that may use the connector 200 (as well as describe exemplary burr hole anchors) is described in more detail in a related U.S. Patent Application entitled EXTERNALLY RELEASABLE BODY PORTAL ANCHORS AND SYSTEMS (U.S. patent application Ser. No. 11/589,697, filed on even date herewith and incorporated by reference herein in its entirety).

Figure 2B:
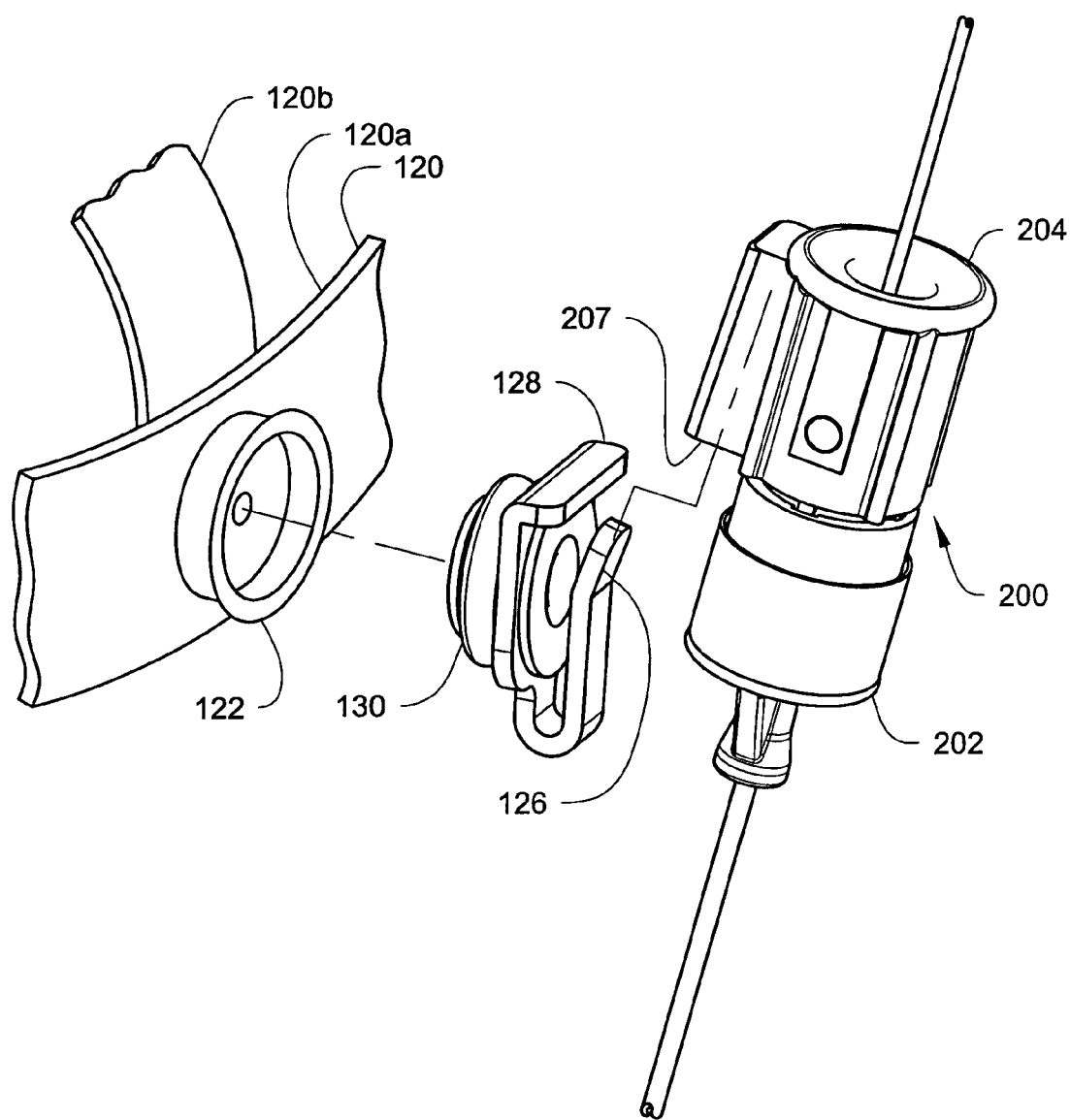

FIG. 2B illustrates one exemplary embodiment for attaching the connector 200 to the headgear apparatus 120. The headgear apparatus may be formed from a series of adjustable, fabric (e.g., nylon webbing) or elastic bands (only two bands 120a and 120b are illustrated in FIG. 2B). The bands may surround the head of the patient, as shown in FIG. 1, sufficiently to reduce or even prevent the headgear apparatus 120 from substantial movement relative to the patient's head. On one or more sides, the headgear apparatus 120 may have attached thereto (e.g., riveted) a circular snap fit receptacle 122 that, in one embodiment, is similar or identical to the female portion of a conventional metallic garment snap button.

The first coupler 204 of the connector 200 may optionally include an integrally formed (or otherwise attached) bracket that forms a receiving slot 207 (shown only in FIG. 2B) along one side. The receiving slot 207 may be configured to receive a tab 126 of a clip 128. Once the tab 126 is fully inserted into the slot 207, the clip 128 may be generally attached to the connector 200 until the components are intentionally disassembled. The clip may also include a male member 130 that is receivable by the snap fit receptacle 122 (the male member 130 may be similar or identical in construction to a male portion of the conventional garment snap button). Once the clip is attached to the receptacle 122, the clip (and thus the connector 200) may pivot generally about an axis of the receptacle, e.g., providing some degree of stress relief to the catheter 108.

Figure 3:
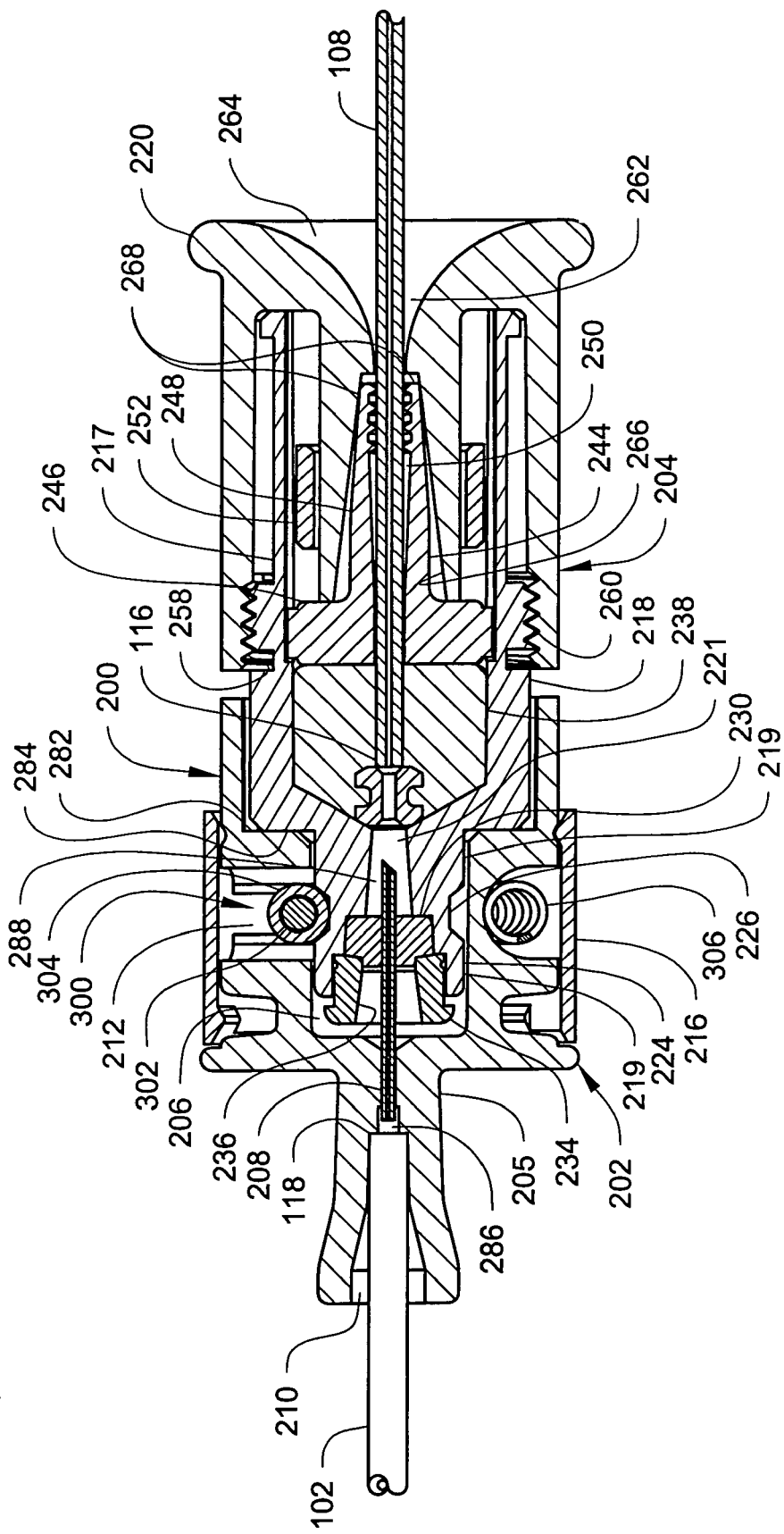
FIG. 3 is a section view of the connector of FIG. 2A, taken through a plane containing an axis of the connector, illustrating both a first coupler and a second coupler.
Figure 4:
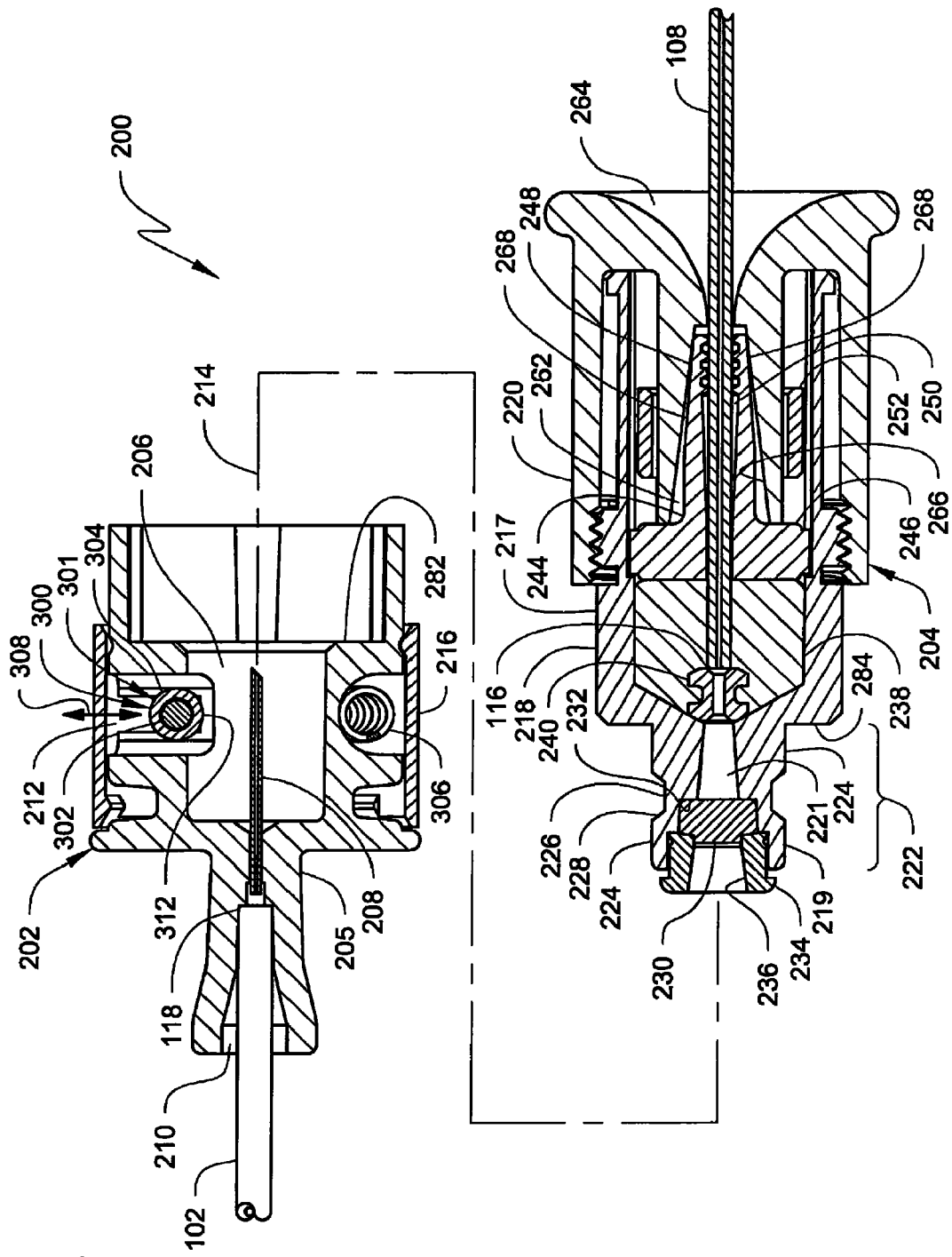
FIG. 4 illustrates the section of the connector shown in FIG. 3 with the first coupler shown separated from the second coupler.

FIG. 3 is a cross sectional view of the connector 200 of FIG. 2A (taken through a plane containing a longitudinal axis of the connector) with the couplers 202 and 204 connected. FIG. 4, on the other hand, is a similar section view with the couplers detached. Each of the couplers 202 and 204 is described separately below with reference to these figures.

The second coupler 202 may form a tubular body 205 defining a bore 206.

The body 205 may be made from various materials including, for example, polyetheretherketone (PEEK), polycarbonate, and similar materials. A hollow needle 208 may be attached to the body 205 and extend into the bore 206 as illustrated. The needle 208 may define a lumen or passageway in fluid communication with the tube 102. The needle 208 may be affixed to the body 205 via any acceptable technique including, for example, by adhesive.

The body 205 also defines a smaller secondary bore 210 configured to receive the tube 102. The tube 102 may attach to the second coupler in a manner similar to the needle 208, e.g., with adhesive. When assembled as illustrated in FIGS. 3 and 4, fluid may travel from the source (e.g., pump 106 of FIG. 1) through a lumen of the tube 102 and through the hollow needle 208.

The connector 200 may further include a retention device, e.g., biased retention device 300, which, in the illustrated embodiment, is attached to, or otherwise associated with, the second coupler 202. The retention device 300, further illustrated in FIGS. 5A and 5B (some structure removed for clarity in these views), may include a roller assembly 301 having an axle 302 and a cylindrical roller 304 rotatable about the axle. A tension member, e.g., spring 306, may also be included and attached to opposite first and second ends of the axle 302. The spring 306 may extend circumferentially about the tubular body 205 of the second coupler 202 as shown.

The roller assembly, e.g., the cylindrical roller 304, may, in a first configuration, be positioned offset from (and preferably transverse to), an axis 214 of the first and second couplers. The axle 302 may be configured to move (e.g., translate) within slots 212 formed in the body 205 such that the axle and roller 304 are movable primarily in a radial direction 308 (see FIGS. 4, 5A, and 5B) from the axis 214 (see FIG. 4) of the couplers. The spring 306, which may be a conventional (e.g., stainless steel) extension spring, may provide a radially-biased force to the axle 302 that tends to pull the roller assembly 301 (e.g., the axle 302 and roller 304), towards the axis 214. The other components of the roller assembly, e.g., the roller 304 and the axle 302 may also be made from stainless steel.

The roller assembly 301 may further include a washer or flange 310. The flange 310, which may be integrally formed with the axle 302, assists with guiding the roller assembly 301 within the slots 212 as shown in FIGS. 5A and 5B.

Figure 5B:
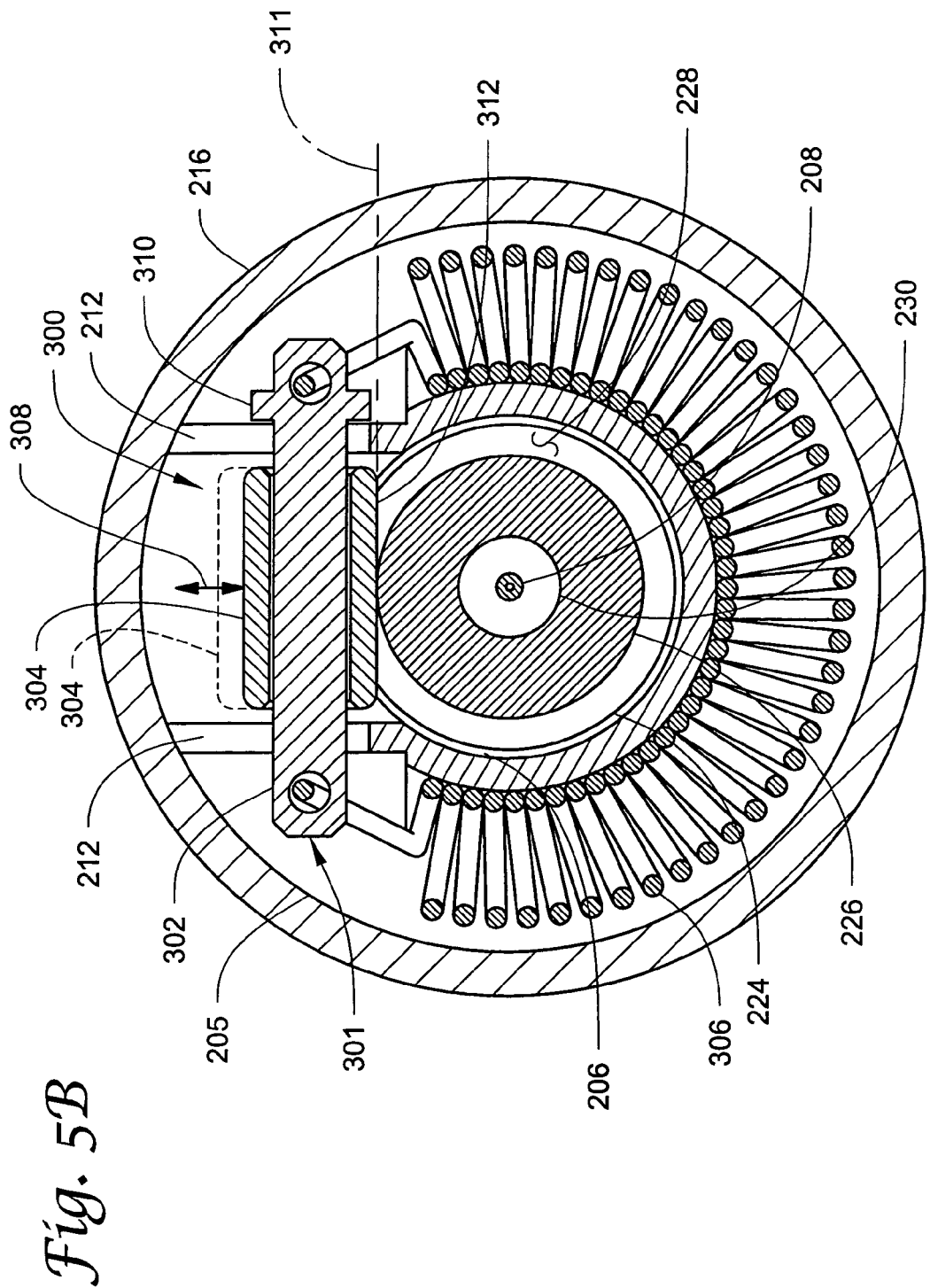

As illustrated in FIG. 5B, the roller assembly 301 of the retention device may also include a contact surface 312 (e.g., the outer surface of the roller 304). The contact surface 312 may, in the illustrated embodiment, form a secant 311 extending through the bore 206 of the tubular body 205 when the roller assembly is in the first configuration shown in solid lines in FIG. 5B (e.g., corresponding to a grooved surface 226 of the first coupler 204 (see FIG. 4) being aligned with the roller 304). As further described below, the roller assembly 301, e.g., the contact surface 312, may move to a second configuration (shown in broken lines in FIG. 5B), wherein the contact surface 312 is located at or outside of the bore 206. Thus, as further described below, the roller assembly 301 may be configured to selectively interlock the second coupler 202 with the first coupler 204; and release the first coupler from the second coupler when a predetermined traction force is applied between the first and second couplers.

The second coupler 202 may further include an optional sleeve 216 that covers at least a portion of the outer surface of the body 205. The sleeve 216 may reduce the potential for patient/clinician contact with portions of the retention device 300, and may further prevent foreign objects from interfering with its operation. Exemplary materials for the sleeve include polyurethane and polypropylene. The sleeve 216 may include a lip (e.g., a discontinuous lip as shown in FIGS. 3 and 4) or other locating feature that permits it to snap or bias into place relative to the body 205.

The first coupler 204 is illustrated in detail in FIGS. 3, 4, 6, and 7A-7C. The first coupler may, in the illustrated embodiment, be formed by an attachment member 218 and a housing 220, both of which may be constructed from materials similar to the body 205 of the second coupler 202.

The attachment member 218 may include an engagement portion 219 receivable within the bore 206 of the second coupler 202. The attachment member 218 may also include a body portion 217 that is threadably engagable with the housing 220. In the illustrated embodiment, the attachment member 218 is, when inserted into the bore 206, coaxial with the second coupler 202.

The engagement portion 219 may include an outer surface 222 having a generally cylindrical cross section. The roller 304 of the roller assembly 301 may be configured to engage the outer surface 222 of the engagement portion 219 in rolling contact as the engagement portion moves, e.g., translates, within the bore 206 of the second coupler 202. The outer surface 222 may be formed by both an engagement surface 224 defined by a first diameter, and the grooved surface 226 (or "groove") defined by a second diameter that is less than the first diameter (see, e.g., FIG. 4). The grooved surface 226 is positioned along the engagement surface 224 so as to receive the roller assembly 301 of the retention device (e.g., the roller 304) when the first coupler 204 is fully engaged with the second coupler 202 as shown in FIG. 3. The phrases "fully engaged," "fully connected,", "fully inserted," and the like are used herein to indicate that the noted components are engaged to a point where further engagement is either not possible or not necessary to the proper functioning of the connector.

The outer surface 222 may further include a ramped surface 228 extending between the grooved surface 226 to the engagement surface 224. The ramped surface 228 may act as a camming surface to permit rolling contact of the roller 304 back and forth between the engagement surface 224 and the grooved surface 226.

The attachment member 218 may form a tubular wall that defines a passageway 221 extending through the attachment member. The passageway 221 may surround or otherwise contain a needle-penetrable septum 230 in the vicinity of the engagement portion 219. The septum 230 may be made of most any material that permits selective penetration by the needle 208 and self-sealing upon needle withdrawal. While other materials are possible, the septum 230 is, in one embodiment, made of silicone.

The septum 230 may be secured within the passageway 221 in most any fashion. For example, in the illustrated embodiment, the passageway 221 may form a step surface 232 (e.g., proximate the engagement portion 219) against which the septum 230 may be located. A retaining member 234 may then be secured (e.g., via adhesive or the like) within the passageway 221 to secure the septum 230 in place. The retaining member 234 may, in one embodiment, have a tapered interior surface 236 that assists in guiding the needle 208 into the septum 230 as the first coupler 204 is connected to the second coupler 202.

The attachment member 218 may be attached to the housing 220 before use as further described below. While the particular attachment technique may vary without departing from the scope of the invention, the body portion 217 of the attachment member may, in the illustrated embodiment, include a threaded portion (e.g., male thread 260) operable to engage a corresponding threaded portion (e.g., female thread 258) of the housing 220 as shown in FIGS. 3, 4, 6, and 7A.

As evident in the figures, the body portion 217 may be of larger diameter that the engagement portion 219 to accommodate various components of the first coupler 204. For example, the body portion 217 may be sized to receive a seal 238 within the passageway 221. The seal 238 preferably includes a lumen that extends completely through the seal. The lumen of the seal may be configured to receive the proximal end 116 of the catheter 108 and form a substantially leak-free seal therewith. In one embodiment, the seal 238 may include a generally compliant body (e.g., made from silicone or similar material) configured to surround the end 116 of the catheter 108, and an optional rigid tubular member 240 positioned within the lumen, e.g., proximate one end of the compliant body. The rigid tubular member 240 may serve various purposes including, for example, preventing occlusion of the lumen of the seal 238 as the seal is compressed. Moreover, the member 240 may provide an abutting surface against which the proximal end 116 of the catheter 108 may seat during assembly of the first coupler 204.

The tubular member 240 may be made from most any material that can hold its shape as the seal 238 is compressed. Exemplary materials include polysulfone and polycarbonate. The tubular member 240 may be attached to the body of the seal (e.g., adhesive, interference fit), or it may be held in place merely by contact between the inner surface of the passageway 221 and a step surface formed in the seal body.

Figure 6:
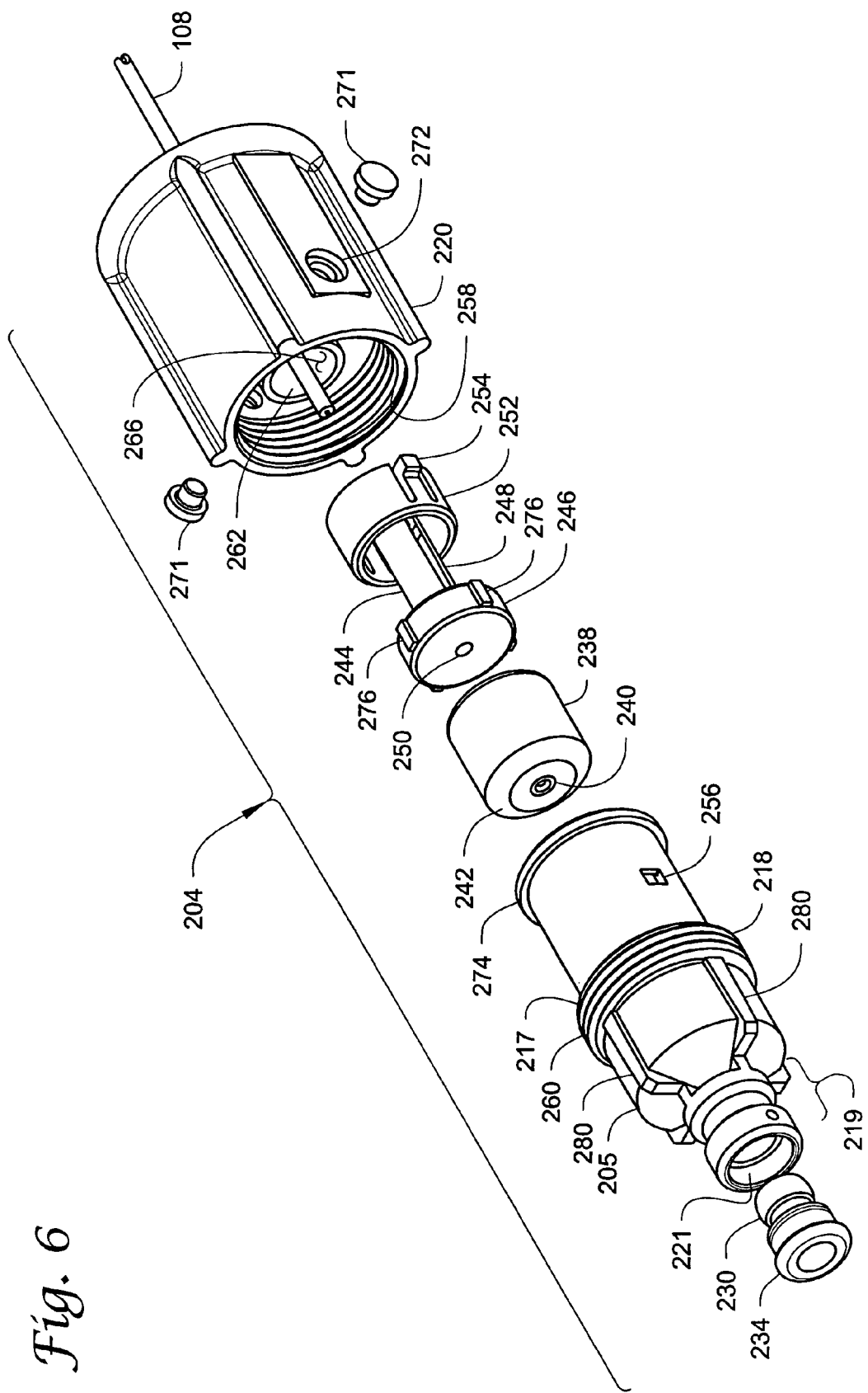
FIG. 6 is an exploded perspective view of the first coupler of the connector of FIG. 2A.

FIG. 6 provides an exploded view of the first coupler 204. As shown in this view, the seal 238 may include a tapered surface 242 to seat against a corresponding tapered surface within the passageway 221 of the attachment member 218 as shown in FIGS. 3 and 4. The first coupler 204 may also include a collet 244 located within the passageway 221 of the attachment member 218. The collet 244 is configured to, in conjunction with the housing 220, compress the seal 238 and clamp or otherwise immobilize the catheter 108. The collet 244 may include a piston 246 that abuts the seal 238, and a split rod 248 operable to receive the catheter 108 therein. The collet 244 may further include a collet passageway 250, extending through the collet (e.g., through the piston 246 and split rod 248), through which the catheter 108 may pass as shown in FIGS. 3 and 4. The collet 244 may be made from a material similar to that of the body 205.

As further described below, the collet 244 may translate within the attachment member 218. To limit the range of travel of the collet, a stop or stop member 252 may be provided. FIG. 6 illustrates that the stop member 252 may include ears 254 (only one shown) configured to engage openings 256 (only one shown) in the body portion 217 of the attachment member 218. Once the ears 254 are engaged with the openings 256, the stop member 252 generally limits travel and prevents removal of the collet 244 from the attachment member 218 (unless the stop member is first removed).

As with the other components of the first coupler 204, the housing 220 may define a passageway 262 extending completely through the component to permit passage of the catheter 108. At the outermost end of the housing 220, e.g., where the catheter exits, the passageway 262 may flare to form a bell-mouth opening 264. The large radius of the bell-mouth opening 264 may reduce strain on the catheter 108 during the implantation period.

The portion of the passageway 262 opposite the bell-mouth opening 264 may form a frusto-conical surface 266 diverging towards the piston 246 of the collet 244 as shown in FIGS. 3 and 4. The frusto-conical surface 266 is configured to contact two or more movable (e.g., deflectable) legs 268 of the split rod 248 of the collet as the housing 220 is threaded onto the attachment member 218. As the surface 266 contacts the legs 268, the legs may be directed inwardly towards the catheter 108. The legs 268 may mechanically (e.g., frictionally or via a biting or clamping action) engage the catheter 108 when the housing 220 is fully engaged with the attachment member 218 as described below. In the illustrated embodiment, the legs 268 may include protrusions 270 (see FIG. 7C) to assist with engagement of the catheter 108.

The frusto-conical surface 266 of the housing may also terminate at an abutting surface configured to contact and push against the piston 246 of the collet 244. As a result, when the housing 220 is fully engaged with, e.g., threaded onto, the attachment member 218, the collet 244 may both compress the seal 238 against an inner surface of the attachment member, and mechanically engage the catheter 108.

FIGS. 6 and 7A-7C illustrate assembly of the first coupler 204. As shown in these views, the septum 230 and retaining member 234 may be secured within the passageway 221 of the attachment member 218 as discussed above. The seal 238, collet 244, and stop member 252 may then be placed into the attachment member 218 and the stop member positioned such that the ears 254 engage the openings 256 as described above. To assist with aligning the stop member 252 with the openings 256, grooves 253 may be provided along the inside surface of the attachment member 218 as shown in FIG. 7C.

Once the seal 238 and collet 244 are positioned, the housing 220 may be placed over the attachment member 218 as shown in FIG. 7A. When the housing 220 is sufficiently engaged with the attachment member 218, optional tabs 271 may be inserted and secured within openings 272 (only one opening shown in FIG. 6). The tabs 271 may protrude past the interior surface of the housing 220 such that, when the housing is unthreaded and withdrawn from the attachment member 218, the tabs engage a raised lip 274 of the attachment member to prevent inadvertent component separation. The tabs 271 may secure to the housing 220 via most any acceptable method including, for example, adhesive or press fit.

As illustrated in the figures, see, e.g., FIG. 7C, the collet 244 may include clocking features (e.g., one or more keys 276 located on the outer surface of the piston 246) that engage the attachment member 218 (engage either or both of the keyways 253 and keyways 278 formed on the inner surface) and prevent relative rotation. The external surface of the attachment member 218 may also include one or more keys 280 (see FIG. 6) that engage corresponding keyways (visible in FIG. 4) on an inner surface of the second coupler 202 to prevent relative rotation of the couplers 202 and 204 during use.

At this point, the catheter 108 may be inserted into the first coupler 204, via the bell-mouth opening 264, until it bottoms out in the seal 238 (e.g., contacts the tubular member 240) as shown in FIG. 7A. The catheter 108 may include markings, e.g., laser markings (not shown), that assist the clinician in determining if the catheter is fully inserted. The housing 220 may then be moved until the female thread 258 engages the male thread 260 of the attachment member 218. Subsequent threading of the housing 220 onto the attachment member 218 results in compression of the seal 238, thereby sealing the fluid path between the first coupler 204 and the catheter 108.

Moreover, relative movement between the housing and attachment member results in engagement of the frusto-conical surface 266 with the legs 268 of the collet 244, which may eventually apply a mechanical force (e.g., a gripping or clamping force) to the catheter 108. The first coupler 204 (e.g., the collet 244) is preferably configured to ensure that the gripping force on the catheter is greater than the intended breakaway force of the connector 200. As a result, when a traction force is applied to the tube 102 and the catheter 108, the couplers 202 and 204 separate before the catheter 108 dislodges from the first coupler.

Preferably, the legs 268 of the collet 244 are configured to engage and grip the catheter 108 only after the seal 238 has been compressed. As a result, axial catheter movement resulting from seal compression may be accommodated before the collet immobilizes the catheter 108.

The catheter 108 may be configured such that it can be satisfactorily immobilized by the collet 244 without occlusion of the fluid passageway. For example, in one embodiment, the catheter could be made from an elastomeric material (pure or blended) such as a polymer, silicone, or the like.

In another embodiment, the catheter 108 may include a tubular core 107 (see, e.g., FIG. 7A) made from flexible tubing that is resistant to compression and collapse, e.g., silica or quartz capillary tubing, PEEK capillary tubing, or stainless steel capillary tubing. The tubular core 107 may have an inner diameter of about 100 micrometers and an outer diameter of about 200 micrometers, e.g., about 193 micrometers. An exemplary core 107 may be a flexible synthetic fused silica capillary having an optional protective polymer (e.g., polyimide) coating such as the TSP line of products sold by Polymicro Technologies, LLC, of Phoenix, Ariz., USA.

A flexible outer covering 109 such as a polyurethane jacket having an outer diameter of about 1 millimeter, and a hardness of about 55 Shore D (at the completion of manufacture) may be formed over the tubular core 107. The flexible outer covering may permit high mechanical clamping/indentation forces to be applied to the catheter, while the tubular core 107 prevents catheter occlusion under such high forces. In some embodiments, the tubular core 107 may protrude longitudinally beyond the flexible outer covering 109 at one or both ends of the catheter, e.g., about 10 mm. In still yet other embodiments, strengthening members, e.g., helically-wound braided members and/or straight longitudinal members, may be sandwiched between the core 107 and the flexible outer covering 109 or embedded within the outer covering. Exemplary strengthening members may include steel, polyester (e.g., polyethylene terepthalate (PET)), synthetic polymers such as Kevlar brand fiber (sold by E. I. du Pont de Nemours of Wilmington, Del., USA), and liquid crystal polymers.

The outer covering 109 may be applied to the tubular core in any known fashion. For example, it may be applied over the core 107 through a secondary extrusion process. Alternatively, the outer covering 109 may form a tube which slides over the tubular core 107 with clearance. A shrink-wrap tube may then be placed over the assembled tubes and the entire assembly heated. Any optional strengthening members, e.g., woven fibers, may also be placed over the tubular core 107 or the outer covering 109 before the heat shrink tube is applied. Subsequent heating of the assembly may cause the outer covering 109 to melt and the shrink-wrap tube to constrict. Thus, the shrink-wrap tube may force the melted outer covering (and optional strengthening members) inwardly towards the tubular core 107 and bond to the same. The shrink-wrap tube may then be removed to produce the catheter 108.

The tube 102, may, on the other hand, be constructed from conventional medical tubing such as polyurethane, silicone, or co-extrusions such as silicone/nylon or silicone/polyurethane. Alternatively, the tube 102 could be made from plasticized polyvinyl chloride (e.g., flexible PVC). In one embodiment, the tube 102 may have an inner diameter of about 0.07 mm to about 0.08 mm (e.g., about 0.076 mm) and an outer diameter of about 1.4 mm to about 1.5 mm (e.g., about 1.47 mm). While exemplary embodiments of the catheter and tube are so described above, variations in material, construction, and size of the catheter 108 and tube 102 are certainly possible without departing from the scope of the invention.

Once the housing 220 is completely threaded onto the attachment member 218, the first coupler 204 is generally configured as shown in FIG. 4. The second coupler 202 may then be positioned proximate the first coupler 204 such that the bore 206 is generally aligned with the engagement portion 219. The engagement portion may then be slid into the bore 206 such that the roller 304 contacts the outer surface 222 of the engagement portion. This contact results in the roller assembly 301, e.g., the roller 304, being displaced outwardly (upwardly in FIG. 4) against the biasing force of the spring 306. The roller 304 may then roll along the engagement surface 224 until it reaches the ramped surface 228, at which point the roller may roll down the ramped surface and engage (contact) the grooved surface 226.

The biasing force of the spring 306 tends to keep the roller assembly 301 engaged with the grooved surface 226 during operation. To prevent backlash in the connector 200, the second coupler 202 and the first coupler 204 may include corresponding abutting surfaces 282 and 284, respectively (see FIG. 4), that contact one another once the couplers are fully connected as shown in FIG. 3.

While not wishing to be bound to any particular embodiment, the roller assembly may utilize an axle 302 having a diameter of about 0.050 inches (in) and the roller 304 (which may be made from acetal resin, PEEK, nylon, or the like) may have an outer diameter of about 0.09 in. In this embodiment, the grooved surface 226 may be recessed about 0.021 in below the engagement surface 224, and the ramped surface 228 may form an angle of about 50 degrees from the engagement surface.

As the second coupler 202 is attached to the first coupler 204, the needle 208 associated with the second coupler may pierce the septum 230 associated with the first coupler 204, thereby providing a fluid path from the second tube 102 to the first tube (e.g., the catheter 108). As a result, therapeutic agent contained in the infusion pump 106 (see FIG. 1) may be delivered to the body through the tube 102 and catheter 108 in accordance with any desired infusion profile.

The retention device 300 is configured to release the first coupler 204 from the second coupler 202 once a predetermined traction force (the "breakaway force") is applied between the couplers, e.g., between the tube 102 and the catheter 108. In the illustrated embodiment, various features affect the breakaway force including, for example, the depth of the grooved surface 226, the angle of the ramped surface 228, the diameter of the roller 304, the friction of the roller about the axle 302, and the spring force of the spring 306. While not wishing to be bound to any particular range of parameters, embodiments of the present invention may provide a connector 200 having a breakaway force of about 1 pound force (lbf) to about 10 lbf and, preferably about 1 lbf to about 5 lbf, and more preferably, about 1.5 lbf to about 3 lbf.

When the predetermined traction force is reached, the roller 304 may move radially outward as it rolls from the grooved surface 226, along the ramped surface 228, to the engagement surface 224. The roller 304 may continue to roll along the engagement surface 224 until the couplers separate.

While described and illustrated herein utilizing the retention device 300, other retention mechanisms are possible without departing from the scope of the invention. For example, FIGS. 8A and 8B illustrate an alternate retention device 400. In this embodiment, the device includes a roller assembly having an axle 402 and a roller 404 rotatable about the axle. The axle 402 may be formed as part of a spring clip, e.g., C-shaped clip 406. The clip 406 may be configured to fit within a circumferential groove 408 formed in the body 410 of a second coupler. The roller 404 may be similarly contained within a slot 412 formed in the body. The body 410, while only partially illustrated in FIGS. 8A and 8B, is understood to be substantially similar to the body 205 of the coupler 202 described above (e.g., it includes a bore 414 to receive the attachment member 218 substantially as described above). A sleeve 416 similar to the sleeve 216 already described herein may also be included.

As with the retention device 300, the roller assembly, e.g., roller 404, may include a contact surface 418 formed by the outer surface of the roller. The contact surface 418 may form a secant through the bore 414 of the tubular body 410 when the roller is in a first position as shown in FIG. 8B. When the attachment member is inserted into the bore 414, the roller 404 may move to a second position (see broken line representation of axle 402) wherein the contact surface is located outside of the bore. Movement of the roller 404 may be accommodated via deflection of the clip 406 as may occur during insertion and removal of the first coupler 204 from the bore 414.

As with the device 300, the device 400 may engage the outer surface 222 of the attachment member 218 (see FIG. 4) in rolling contact. Moreover, the roller 402 may be biased in a generally radial direction to maintain rolling contact with the attachment member 218 of the first coupler during insertion/removal.

Connectors in accordance with embodiments of the present invention provide tubing/catheter couplers that breakaway or separate from one another when a predetermined traction force is applied to the couplers and/or to their associated tubes. Moreover, the retention device that interconnects the two couplers may minimize frictional engagement therebetween by providing rolling contact engagement. As a result, the breakaway force required to separate the couplers is substantially repeatable, avoiding the variability commonly associated with friction-based retention interfaces. Connectors in accordance with embodiments of the present invention further provide an upstream coupler (e.g., a coupler attached to an implanted catheter) that minimizes exposure to contamination even when the couplers of the connector separate. Accordingly, replacement or sterilization of the upstream catheter and/or coupler may be unnecessary in the event inadvertent separation of the connector occurs.

Connectors in accordance with embodiments of the present invention further provide a fluid flow path with minimal dead volume (the static volume that is filled before fluid is transferred through the connector). Reduced dead volume is advantageous as it may decrease the volume of wasted therapeutic agent. In the illustrated embodiment of FIG. 3, the connector (e.g., the region 286 between the second tube 102 and the needle 208, and the region 288 between the septum 230 and the seal 238) is designed to provide a low dead volume. For instance, connectors in accordance with embodiments of the present invention may have a dead volume of less than 20 microliters, and preferably less than 10 microliters, e.g., nominally about 7 microliters.

The complete disclosure of the patents, patent documents, and publications cited in the Background, the Detailed Description of Exemplary Embodiments, and elsewhere herein are incorporated by reference in their entirety as if each were individually incorporated.

Illustrative embodiments of this invention are discussed and reference has been made to possible variations within the scope of this invention. These and other variations, combinations, and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

What is claimed is:

1. A connector for coupling a first tube to a second tube, the connector comprising:
   a first coupler comprising an engagement portion;
   a second coupler comprising a tubular body defining a bore to receive the engagement portion of the first coupler; and
   a roller assembly associated with the second coupler, the roller assembly comprising a cylindrical roller that, in a first configuration, is offset from an axis of the second coupler, wherein the cylindrical roller is configured to engage an outer surface of the engagement portion in rolling contact as the engagement portion translates within the bore of the tubular body, and wherein the roller assembly further comprises: an axle about which the cylindrical roller rotates; and a spring attached to opposite ends of the axle and extending circumferentially about the tubular body.

2. The connector of claim 1, wherein the outer surface of the engagement portion comprises an engagement surface defined by a first diameter, and a grooved surface defined by a second diameter that is less than the first diameter, the grooved surface positioned along the engagement surface so as to receive the cylindrical roller when the first coupler is fully engaged with the second coupler.

3. The connector of claim 2, wherein the outer surface of the engagement portion further comprises a ramped surface extending between the grooved surface and the engagement surface.

4. The connector of claim 1, wherein the roller assembly is radially-biased towards the axis of the second coupler.

5. The connector of claim 1, wherein the roller assembly is configured to: selectively interlock the first coupler with the second coupler; and release the first coupler from the second coupler when a predetermined traction force is applied between the first and second couplers.

6. The connector of claim 1, wherein the cylindrical roller, when in the first configuration, is transverse to the axis of the second coupler.

7. A connector for coupling a first tube to a second tube, the connector comprising:
   a first coupler comprising an engagement portion;
   a second coupler comprising a tubular body defining a bore to receive the engagement portion of the first coupler, wherein the second coupler further comprises a hollow needle defining a passageway in fluid communication with the second tube, the hollow needle extending into the bore of the tubular body; and
   a roller assembly associated with the second coupler, the roller assembly comprising a cylindrical roller that, in a first configuration, is offset from an axis of the second coupler, wherein the cylindrical roller is configured to engage an outer surface of the engagement portion in rolling contact as the engagement portion translates within the bore of the tubular body.

8. The connector of claim 7, wherein the engagement portion of the first coupler comprises a tubular wall surrounding a needle-penetrable septum.

9. A connector for coupling a first tube to a second tube, the connector comprising:
   a first coupler comprising an engagement portion;
   a second coupler comprising a tubular body defining a bore to receive the engagement portion of the first coupler; and
   a roller assembly associated with the second coupler, the roller assembly comprising a cylindrical roller that, in a first configuration, is offset from an axis of the second coupler, wherein the cylindrical roller is configured to engage an outer surface of the engagement portion in rolling contact as the engagement portion translates within the bore of the tubular body, and wherein the cylindrical roller comprises a contact surface that forms a secant extending through the bore of the tubular body when the cylindrical roller is in the first configuration.

10. A medical tubing connector comprising:
    a first coupler attached to a first tube, the first coupler comprising an attachment member having an engagement portion;
    a second coupler attached to a second tube, the second coupler comprising a tubular body defining a bore to receive the engagement portion of the attachment member; and
    a biased retention device attached to the second coupler and movable from a first configuration, wherein a contact surface formed by the retention device forms a secant extending through the bore of the second coupler, to a second configuration, wherein the contact surface of the retention device is located at or outside of the bore, and wherein the retention device comprises:
      an axle comprising first and second ends;
      a tension member extending circumferentially about the tubular body and attached to the first and second ends of the axle; and
      a cylindrical roller rotatable about the axle.

11. The connector of claim 10, wherein the engagement portion of the attachment member comprises an outer surface, the outer surface comprising an engagement surface and a grooved surface, the grooved surface positioned to receive the retention device when the first coupler is fully engaged with the second coupler.

12. The connector of claim 10, wherein the retention device is configured to: selectively interlock the first coupler with the second coupler; and release the first coupler from the second coupler when a predetermined traction force is applied between the first and second couplers.

13. A medical tubing connector comprising:
    a first coupler attached to a first tube, the first coupler comprising an attachment member having an engagement portion, wherein the first coupler further comprises:
      a housing threadably engagable with the attachment member;
      a seal located within a passageway of the attachment member, the seal operable to receive an end of the first tube; and
      a collet located within the passageway of the attachment member, the collet defining a collet passageway through which the first tube may pass;
    a needle-penetrable septum positioned within the passageway of the attachment member;
    a second coupler attached to a second tube, the second coupler comprising a tubular body defining a bore to receive the engagement portion of the attachment member; and
    a biased retention device attached to the second coupler and movable from a first configuration, wherein a contact surface formed by the retention device forms a secant extending through the bore of the second coupler, to a second configuration, wherein the contact surface of the retention device is located at or outside of the bore.

14. The connector of claim 13, wherein the collet comprises one or more movable legs configured to mechanically engage the first tube when the housing is fully engaged with the attachment member.

15. The connector of claim 13, wherein the collet is configured to compress the seal against an inner surface of the attachment member when the housing is fully engaged with the attachment member.

16. The connector of claim 13, wherein the seal comprises:
    a body configured to surround an end of the first tube, the body defining a lumen; and
    a rigid tubular member positioned within the lumen of the body.

17. A method for connecting a first tube to a second tube, the method comprising:
    positioning a first coupler attached to the first tube proximate a second coupler attached to the second tube such that a bore of the second coupler is aligned with an engagement portion of the first coupler;
    sliding the engagement portion of the first coupler into the bore of the second coupler, wherein a biased cylindrical roller associated with the second coupler contacts an engagement surface of the engagement portion;
    engaging the cylindrical roller with a grooved surface formed in an outer surface of the engagement portion when the engagement portion is fully inserted into the bore of the second coupler; and
    piercing a septum located within the first coupler with a needle associated with the second coupler.

18. A method for connecting a first tube to a second tube, the method comprising:
    positioning a first coupler attached to the first tube proximate a second coupler attached to the second tube such that a bore of the second coupler is aligned with an engagement portion of the first coupler;

sliding the engagement portion of the first coupler into the bore of the second coupler, wherein a biased cylindrical roller associated with the second coupler contacts an engagement surface of the engagement portion;

engaging the cylindrical roller with a grooved surface formed in an outer surface of the engagement portion when the engagement portion is fully inserted into the bore of the second coupler; and separating the first coupler from the second coupler by applying only a traction force between the first tube and the second tube.

19. The method of claim 18, wherein separating the first coupler from the second coupler comprises rolling the cylindrical roller along a ramped surface extending from the grooved surface to the engagement surface.

* * * * *